United States Patent

Nakamura et al.

Patent Number: 5,498,754
Date of Patent: Mar. 12, 1996

[54] PROCESS FOR REFINING CRUDE FLUOROALKYLSULFONIC ACID WITH THE USE OF WATER

[75] Inventors: Tamio Nakamura; Takashi Yokoyama, both of Ube; Yoshiyuki Kobayashi, Yokohama, all of Japan

[73] Assignee: Central Glass Co., Ltd., Yamaguchi, Japan

[21] Appl. No.: 228,872

[22] Filed: Apr. 18, 1994

[30] Foreign Application Priority Data

Apr. 19, 1993 [JP] Japan .................................. 5-091040

[51] Int. Cl.$^6$ ............................................. C07C 309/04
[52] U.S. Cl. ......................................... 562/113; 562/124
[58] Field of Search .................................... 562/113, 124

[56] References Cited

U.S. PATENT DOCUMENTS 4,927,962  5/1990  Aramaki et al. ................... 562/113

Primary Examiner—José G. Dees
Assistant Examiner—Rosalynd A. Williams
Attorney, Agent, or Firm—Wenderoth, Lind & Ponack

[57] ABSTRACT

A process for refining a crude fluoroalkylsulfonic acid represented by the general formula $RfSO_3H$ wherein Rf is a fluoroalkyl group having 1 to 4 carbon atoms into a highly refined one substantially free of impurities, said process comprising the steps of: (a) providing said crude fluoroalkylsulfonic acid, (b) mixing said crude fluoroalkylsulfonic acid with water or said water and an active silica to obtain a mixture, (c) stirring said mixture while maintaining said mixture at a higher temperature than room temperature, and (d) subjecting the mixture treated in said step (c) to distillation.

24 Claims, No Drawings

PROCESS FOR REFINING CRUDE FLUOROALKYLSULFONIC ACID WITH THE USE OF WATER

FIELD OF THE INVENTION

The present invention relates to a process for producing high purity fluoroalkylsulfonic acids useful as catalysts in organic synthesis reactions or as the starting materials in the production of various fluoroalkylsulfonates. Particularly, the present invention relates to a process for refining crude fluoroalkylsulfonic acids into highly refined fluoroalkysulfonic acids substantially free of contaminants such sulfuric acid and free fluorine components.

RELATED BACKGROUND ART

It is known that fluoroalkylsulfonic acids, which can be represented by the general formula $RfSO_3H$ (with Rf being a fluoroalkyl group), are used as catalysts in various organic reactions but also as the starting materials in the production of various fluoroalkylsulfonates. For instance, trifluoromethanesulfonic acid ($CF_3SO_3H$) belonging to the $RfSO_3H$ is generally used as the starting material in the production of lithium trifluoromethanesulfonate ($CF_3SO_3Li$) which is used in an electrolyte for a lithium battery. The production of the lithium trifluoromethanesulfonate for the lithium battery is conducted by providing a high purity trifluoromethanesulfonic acid and subjecting the trifluoromethanesulfonic acid to neutralization reaction with a high purity lithium carbonate. The neutralization reaction in this case can be expressed by the following formula:

$$2CF_3SO_3H + Li_2CO_3 \rightarrow 2CF_3SO_3Li + CO_2 + H_2O \qquad (1)$$

In this case, it is required for the trifluoromethanesulfonic acid ($CF_3SO_3H$) as the starting material to be as pure as possible such that the content of impurities such as sulfuric acid, free fluorine and the like contained is at a level of the order of a ppm.

The production of the $RfSO_3H$ on an industrial scale may be conducted, for instance, in accordance with a process disclosed in Japanese Patent Publication No. 4218/1955 (hereinafter referred to as Literature 1) as will be described below.

The process described in Literature 1 comprises the following three steps. That is, in a first step, an alkylsulfonylhalide represented by the general formula $RSO_2X$ (with R being a non-substitutedalkyl group and X being Cl or F) is provided, and the $RSO_2X$ compound is subjected to electrolysis in the presence of hydrogen fluoride (HF) to obtain a fluoroalkylsulfonylhalide. This first step can be expressed by the following reaction formula (2), wherein a non-substituted alkylsulfonylfluoride ($R\ SO_2F$) is used as the $RSO_2X$ and, fluoroalkylsulphonylfluoride is obtained as a reaction product.

$$RSO_2F + n\ HF \rightarrow RfSO_2F + n/2\ H_2\uparrow + n/2\ HF \qquad (2)$$

In a second step, the fluoroalkylsulfonylfluoride ($RfSO_2F$) obtained in the first step is subjected to hydrolysis using a KOH solution to obtain a potassium fluoroalkylsulfonate ($RfSO_3K$). This second step can be expressed by the following chemical reaction formula (3).

$$RfSO_2F + 2\ KOH \rightarrow RfSO_3K + KF + H_2O \qquad (3)$$

In a third step, the potassium fluoroalkylsulfonate ($RfSO_3K$) obtained in the second step is mixed with an excessive amount of concentrated sulfuric acid (of 100% in concentration) and if necessary, additionally fuming sulfuric acid, followed by vacuum distillation while heating, to thereby obtain a crude fluoroalkylsulfonic acid ($RfSO_3H$) as a final product. This third step can be expressed by the following reaction formula (4).

$$RfSO_3K + H_2SO_4 \rightarrow RfSO_3H + KHSO_4 \qquad (4)$$

The fluoroalkylsulfonic acid ($RfSO_3H$) obtained is not pure enough and is contaminated with a distinguishable amount of impurities including sulfuric acid and free fluorine components. Therefore, it is necessary to be refined by subjecting it to rectification. However, it is difficult for the fluoroalkylsulfonic acid to be purified as desired for the following reasons.

In the process described in Literature 1, as above described, since the final step (that is, the third step) is conducted by adding concentrated sulfuric acid and if necessary, additionally fuming sulfuric acid in an excessive amount to the potassium fluoroalkylsulfonate ($RfSO_3K$) obtained in the second step to obtain a mixture, and subjecting the mixture to vacuum distillation while heating the mixture, not only a thermal decomposition reaction expressed by the following reaction formula (5) but also side reactions expressed by the following reaction formulas (6) and (7) are unavoidably occurred, to thereby cause a distinguishable amount of impurities including sulfuric acid and free fluorine components, wherein these impurity components are eventually contaminated into the resulting fluoroalkylsulfonic acid ($RfSO_3H$). It is extremely difficult to remove such impurities from the fluoroalkylsulfonic acid in the rectification step. Thus, there is a problem in the process of Literature 1 in that it is extremely difficult to obtain a high purity product of fluoroalkylsulfonic acid ($RfSO_3H$) substantially free of those impurity components as above described.

$$CF_3SO_3H \rightarrow COF_2\uparrow + SO_2\uparrow + HF\uparrow \qquad (5)$$

$$2\ CF_3SO_3H + SO_3 \rightarrow CF_3SO_2.OCF_3\uparrow + SO_2\uparrow + H_2SO_4 \qquad (6)$$

$$2\ CF_3SO_3H + SO_3 \rightarrow (CF_3SO_2)_2 + H_2SO_4 \qquad (7)$$

In order to eliminate the problems in the process of Literature 1, the present inventors previously proposed a process which enables one to refin a crude fluoroalkylsulfonic acid ($RfSO_3H$) accompanied by the foregoing impurities such as sulfuric acid and free fluorine components into a refined one (see, Japanese Patent Laid-open No. 85946/1989 (hereinafter referred to as Literature 2). Particularly, the process of Literature 2 comprises the steps of mixing a crude fluorocarbon compound (specifically, a crude floroalkylsulfonic acid) with sulfuric acid and an active silica to obtain a mixture, subjecting the mixture to heat treatment (that is, decomposition treatment with sulfuric acid) at an elevated temperature under pressure condition while stirring the mixture, and subjecting the resultant to vacuum distillation, to thereby obtain a refined fluoroalkylsulfonic acid ($RfSO_3H$) having an improved purity with a slight content of free fluorine components (HF). In the process of Literature 2, the free fluorine components contained in the crude fluoroalkylsulfonic acid can be removed because of the use of the active silica, which serves to chemically react with the free fluorine components to afford gaseous $SiF_4$ capable of being readily removed at the time of the distillation. Thus, the process of Literature 2 is effective in terms of preventing free fluorine components from contaminating into the resulting refined fluoroalkylsulfonic acid. However, there is still a problem for the process of Literature 2 in that although the contamination of free fluorine components into the resulting sulfuric acid can be prevented, a relatively large amount of sulfuric acid components is still liable to contaminate the resulting refined fluoroalkylsulfonic acid even if the vacuum distillation should be conducted by using a packed column or plate column. In addition to this problem, there is also a problem in the process of Literature 2 in that there is a tendency of causing $HSO_3F$ by way of a chemical reaction expressed by the following reaction formula: $H_2SO_4 + HF \rightleftharpoons HSO_3F + H_2O$, wherein the $HSO_3F$ is sometimes remained without being removed upon the distillation, resulting in contaminating into the resulting refined fluoroalkylsulfonic acid.

SUMMARY OF THE INVENTION

The principal object of the present invention is to eliminate the foregoing problems not only in the process of Literature 1 but also in the process of Literature 2 and to provide an improved process which enables one to produce high purity fluoroalkylsulfonic acids ($RfSO_3H$) which are substantially free of impurities including sulfuric acid and free fluorine components.

Another object of the present invention is to provide an improvement in the conventional process comprising the steps of obtaining a fluoroalkylsulfonylfluoride by reacting a corresponding non-substituted alkylsulfonylfluoride with hydrogenfluoride, subjecting the fluoroalklysulfonylfluoride to hydrolysis using potassium hydroxide to obtain a potassium fluoroalkylsulfonate, subjecting the potassium fluoroalkylsulfonate to decomposition treatment using sulfuric acid to obtain a crude fluoroalkylsulfonic acid, and subjecting the crude fluoroalkylsulfonic acid to vacuum distillation to thereby obtain a refined fluoroalkylsulfonic acid, the improvement comprising subjecting the crude fluoroalkysulfonic acid to stirring treatment with a relatively large amount of water at a relatively high temperature and under condition of atmospheric pressure or reduced pressure to obtain a stirred mixture, and subjecting the mixture to simple vacuum distillation to thereby obtain a high purity fluoroalkylsulfonic acid substantially free of impurities including sulfuric acid and free fluorine components.

A further object of the present invention is to a provide an improved process which enables one to refine a crude fluoroalkylsulfonic acid ($RfSO_3H$) accompanied by impurities including sulfuric acid and free fluorine components, which is produced by the conventional fluoroalkylsulfonic acid-producing process, into a high purity fluoroalkylsulfonic acid substantially free of the foregoing impurities in a simple manner.

A still further object of the present invention is to provide an improvement in the conventional process comprising mixing a crude floroalkylsulfonic acid with sulfuric acid and an active silica to obtain a mixture, subjecting the mixture to decomposition treatment with sulfuric acid at an elevated temperature under pressure condition while stirring the mixture, and subjecting the resultant to vacuum distillation whereby obtaining a refined fluoroalkylsulfonic acid, the improvement comprising subjecting the crude fluoroalkysulfonic acid to stirring treatment with a relatively large amount of water at a relatively higher temperature and under condition of atmospheric pressure or reduced pressure to obtain a treated mixture, and subjecting the mixture to simple vacuum distillation to thereby obtain a high purity fluoroalkylsulfonic acid substantially free of impurities including sulfuric acid and free fluorine components.

DETAILED DESCRIPTION OF THE INVENTION AND THE PREFERRED EMBODIMENTS

The present inventors made extensive studies in order to eliminate the foregoing problems in the prior art of producing a fluoroalkylsulfonic acid and in order to attain the objects of the present invention. Particularly, disregarding the common knowledge in the prior art that the water content in the system containing a crude fluoroalkylsulfonic acid upon conducting the refinement of the crude fluoroalkylsulfonic acid should be reduced as much as possible in terms of preventing contamination of impurities based on the water into the resulting refined fluoroalkylsulfonic acid, the present inventors intentionally attempted to conduct a manner of subjecting a crude fluoroalkylsulfonic acid to stirring treatment in the presence of a relatively large amount of water at a relatively high temperature and under condition of atmospheric pressure or reduced pressure, and subjecting the stirred resultant to vacuum simple distillation. As a result, there was obtained a finding that in accordance with this manner, an unexpectedly highly refined fluoroalkylsulfonic acid which is substantially free of free fluorine components and whose contamination of sulfuric acid components is extremely slight can be effectively obtained.

The present invention has been accomplished based on this finding. The present invention typically includes the following two typical embodiments.

A first embodiment of the present invention is directed to an improvement in a process for producing a fluoroalkylsulfonic acid represented by the general formula $RfSO_3H$ with Rf being a fluorine-substituted lower alkyl having 1 to 4 carbon atoms, comprising the steps of (a) providing an alkylsulfonylhalide represented by the general formula $RSO_2F$ with R being a non-substituted lower alkyl having 1 to 4 carbon atoms, (b) subjecting said $RSO_2F$ compound to electrolytic fluorination using hydrogen fluoride (HF) to obtain a fluoroalkylsulfonylfluoride represented by the general formula $RfSO_2F$ with Rf being a fluorine-substituted lower alkyl having 1 to 4 carbon atoms, (c) subjecting said $RfSO_2F$ compound to hydrolysis using potassium hydroxide (KOH) to obtain a potassium fluoroalkylsulfonate represented by the general formula $RfSO_3K$, (d) subjecting said potassium fluoroalkylsulfonate to acid decomposition reaction with the use of concentrated sulfuric acid to obtain a crude fluoroalkylsulfonic acid represented by the general formula $RfSO_3H$, and (e) subjecting said crude fluoroalkylsulfonic acid to vacuum distillation, the improvement comprising the steps of (1) mixing said crude fluoroalkylsulfonic acid with a relatively large amount of water to obtain a mixture, (2) subjecting the mixture obtained to stirring treatment wherein the mixture is stirred at a relatively high temperature and under condition of atmospheric pressure or reduced pressure for a certain period of time to obtain a treated mixture, and (3) subjecting the treated mixture obtained in said stirring treatment to vacuum distillation, to thereby obtain a highly refined fluoroalkylsulfonic acid substantially free of impurities including sulfuric acid and free fluorine components.

A second embodiment of the present invention is directed to an improvement in a process for refining a crude fluoroalkylsulfonic acid ($RfSO_3H$), comprising (i) providing a crude floroalkylsulfonic acid (RfSO$_3$H), (ii) mixing said crude fluoroalkylsulfonic acid with sulfuric acid and an active silica to obtain a mixture, (iii) subjecting the mixture to heat treatment at an elevated temperature under pressure condition while stirring the mixture, and (iv) subjecting the resultant to vacuum distillation whereby obtaining a refined fluoroalkylsulfonic acid, the improvement comprising the steps of (1) mixing said mixture obtained in said step (ii) with a relatively large amount of water to obtain a mixture, (2) subjecting the resultant mixture to stirring treatment wherein the mixture is stirred at a relatively high temperature and under condition of atmospheric pressure or reduced pressure for a certain period of time to obtain a treated mixture, and (3) subjecting the resultant treated mixture obtained in said stirring treatment to vacuum distillation, to thereby obtain a highly refined fluoroalkylsulfonic acid substantially free of impurities including sulfuric acid and free fluorine components.

In the second embodiment, the crude fluroalkylsulfonic acid may be one produced by the process of Literature 1.

According to the present invention, there can be effectively obtained high purity fluoroalkylsulfonic acids which are desirably usable as catalysts in various organic reactions upon the production of various chemical compounds. Especially, the present invention enables one to effectively produce high purity trifluoromethanesulfonic acid (CF$_3$SO$_3$H) capable of providing high purity lithium trifluoromethanesulfonate (CF$_3$SO$_3$Li), which is desirably usable in the production of an electrolyte for a lithium battery.

In any of the first and second embodiments of the present invention, the stirring treatment step (2) is desired to be conducted preferably at a higher temperature than room temperature, more preferably at a temperature in the range of from 60° C. to 300° C. And it is desired for the stirring treatment step to be conducted for a period of time of at least 30 minutes.

As above described, in the process of Literature 1, impurities including sulfuric acid and free fluorine components are unavoidably contaminated into the fluoroalkylsulfonic acid afforded in the step of decomposing the potassium fluoroalkylsulfonate with the use of concentrated sulfuric acid, and these impurities contained in the fluoroalkysulfonic acid are extremely difficult to be removed upon the vacuum distillation step. However, these problems in the process of Literature 1 are effectively eliminated according to the present invention, wherein such crude fluoroalkylsulfonic acid contaminated with impurities including sulfuric acid and free fluorine components are distilled in the presence of a relatively large amount of water wherein the impurities are effectively and markedly removed, resulting in affording a highly refined fluoroalkylsulfonic acid substantially free of the impurities. Especially, in the case where the crude fluoroalkylsulfonic acid is a crude trifluoromethanesulfonic acid (CF$_3$SO$_3$H), the water added is dedicated to react with sulfuric components to form a hydrate (CF$_3$SO$_3$H.H$_2$O) having a relatively high boiling point (b.p.=217° C.) and a melting point of 34° C. On the other hand, CF$_3$SO$_3$H is of b.p.=161° C. and m.p.=−40° C. Because of the difference between the two in terms of the boiling point, the hydrate (CF$_3$SO$_3$H.H$_2$O) becomes a residue upon conducting the distillation, and it is effectively removed. Therefore, the distillate of trifluoromethanesulfonic acid (CF$_3$SO$_3$H) obtained is substantially free of sulfuric acid and free fluorine components. Especially in the case where the crude trifluoromethanesulfonic acid (CF$_3$SO$_3$H) is refined in accordance with the process of the second embodiment of the present invention, it is extremely highly refined to be substantially free of not only sulfuric acid components but also free fluorine components.

In the process of the second embodiment of the present invention, the presence of water in relatively large amounts in the mixture comprising the crude fluoroalkylsulfonic acid, sulfuric acid, and active silica upon the stirring treatment is effective to not only prevent occurrence of the foregoing reaction of causing HSO$_3$F but also to effectively prevent sulfuric acid components from contaminating the resulting refined fluoroalkylsulfonic acid. Hence there is afforded a high purity fluoroalkylsulfonic acid substantially free of impurities including sulfuric acid and fluorine components.

In the present invention, as for the amount of the water to be used in the stirring treatment step, it is preferably in the range of from 0.1 to 30 wt. %, more preferably in the range of from 0.5 to 4 wt. %, versus the sum amount of all the materials involved in the stirring treatment. In the case where the amount of the water to be used is less than 0.1 wt. %, sufficient removal of the sulfuric acid components upon the distillation cannot be attained as desired. On the other hand, in the case where the amount of the water to be used exceeds 30 wt. %, a problem entails in that an excessive amount of water is liable to incorporate into a distillate of fluoroalkylsulfonic acid obtained by the distillation.

The present invention is particularly effective for refining a crude fluoroalkysulfonic acid (RfSO$_3$H) produced by the manner of subjecting a potassium fluoroalkylsulfonate (RfSO$_3$K) to decomposition reaction with sulfuric acid. However, the present invention is also applicable in the refinement of other crude fluoroalkylsulfonic acids produced from (RfSO$_3$)$_n$M with Rf being the same meaning as the above Rf, M being a metal other than K, or NH$_4$, and n being an integer, wherein the effects of the present invention are also provided as desired.

The active silica used in the present invention can include silica compounds which are readily reactive with free fluorine components. Specific examples of such silica compound are silica compounds obtained from diatomaceous earth materials, sodium silicate, silicon fluoride, and mixtures of these compounds. In the present invention, it is possible to use an appropriate glassy material which is readily reactive with free fluorine components, instead of the active silica. The glassy material can include various silicate glasses.

As for the active silica to be added, it is desired to be an amount corresponding to a figure of 2 to 100 in terms of the reaction equivalent weight ratio of SiO$_2$/4HF in the chemical reaction represented by the following reaction formula (8), wherein SiO$_2$ indicates an active silica and HF indicates a free fluorine component contained in a crude fluoroalkylsulfonic acid.

$$SiO_2 + 4HF \rightarrow 2H_2O + SiF_4 \uparrow \qquad (8)$$

In the case where the amount of the active silica to be added is less than the lower limit of the above range, the chemical reaction (8) is not sufficiently occurred and as a result, a certain amount of free fluorine components (HF) is remained and contaminated into the resulting refined fluoroalkylsulfonic acid. On the other hand, the addition of the active silica in an excessive amount beyond the upper limit of the above range is not economical since the removal of free fluorine components is performed within the above range in terms of the amount of the active silica to be added.

In the above, description has been made chiefly to the removal of sulfuric acid and free fluorine components as the impurities contained in a crude fluoroalkylsulfonic acid.

As for the crude fluoroalkylsulfonic acid ($RfSO_3H$) produced by subjecting a corresponding potassium fluoroalkysulfonate ($RfSO_3K$) to decomposition with sulfuric acid, specifically when it is a crude trifluorometanesulfonic acid ($CF_3SO_3H$), it is often contaminated with, in addition to the foregoing sulfuric acid and free fluorine components, other impurities such as $SO_3$, $S_2O_3$, $HSO_3F$, $COF_2$, and $CF_3SO_2.OCF_3$, and in addition to these, occasionally also $(CF_3SO_2)_2O$ in a trace amount. According to the present invention, these impurities contained in the crude trifluoromethanesulfonic acid are effectively removed because the presence of a relatively large amount of water in the stirring treatment step functions to cause various hydrolytic reactions represented by the following reaction equations (9) to (13) even at room temperature, resulting in facilitating removal of these impurities in the stirring treatment step or/and the distillation step, whereby a highly refined, high purity fluoroalkylsulfonic acid ($RfSO_3H$) substantially free of not only the foregoing sulfuric acid and free fluorine components but also those impurities as above described is obtained.

$$SO_3+H_2O \rightarrow H_2SO_4 \qquad (9)$$

$$S_2O_3+H_2O \rightarrow H_2SO_4+S \qquad (10)$$

$$HSO_3F+H_2O \rightarrow H_2SO_4+HF \qquad (11)$$

$$COF_2+H_2O \rightarrow CO_2\uparrow +2HF \qquad (12)$$

$$(CF_3SO_2)_2O+H_2O \rightarrow 2CF_3SO_3H \qquad (13)$$

Particularly, as for the impurity $SO_3$, it is reacted with the water to convert into sulfuric acid ($H_2SO_4$) as shown in the reaction formula (9), and the sulfuric acid is readily removed in the successive distillation step. As for the impurity $HSO_3F$, it is reacted with the water to produce sulfuric acid ($H_2SO_4$) and hydrogen fluoride (HF) as shown in the reaction formula (11). The sulfuric acid caused therein is readily removed in the successive distillation step as well as in the above case. As for the impurity $COF_2$, it is reacted with the water to produce gaseous $CO_2$ and hydrogen fluoride (HF). The gaseous $CO_2$ caused is readily removed outside the system in the stirring treatment step. As for the HF caused in the reactions (11) and (12), it is partly in a gaseous state and partly in a state resolved in the mixture in the stirring treatment step. The gaseous HF portion is readily removed outside the system in the stirring treatment step. The remaining HF portion resolved in the mixture is readily removed in the successive distillation step. In the case where an active silica is present in the stirring treatment step, the remaining HF portion resolved in the mixture is reacted with the active silica to convert into gaseous $SiF_4$, which is readily removed outside the system in the stirring treatment step. As for the impurity $(CF_3SO_2)_2O$, it is reacted with the water to advantageously convert it into trifluoromethanesulfonic acid ($CF_3SO_3H$) as shown in the reaction formula (13).

As for the impurity $S_2O_3$ (disulfur trioxide), when this compound is contained in the resulting refined fluoroalkylsulfonic acid ($RfSO_3H$) (specifically, the resulting refined trifluoromethanesulfonic acid) even at a trace content of a single digit ppm, it is colored in bluish green. The $S_2O_3$ as the impurity is therefore necessary to be removed also in this viewpoint. As shown in the reaction formula (10), the $S_2O_3$ is reacted with the water to produce sulfuric acid ($H_2SO_4$) and sulfur (S). The sulfuric acid caused here is readily removed in the successive distillation step as well as in the above case. As for the sulfur (S), it is in a solid state and because of this, it is readily removed as a residue on distillation in the successive distillation step.

The impurity $S_2O_3$ contained in the crude fluoroalkylsulfonic acid ($RfSO_3H$) may be removed by subjecting the crude fluoroalkylsulfonic acid to heat treatment at a temperature in the range of from 40° C. to 100° C. to thereby decompose the $S_2O_3$ into SO, $SO_2$ and S, wherein the SO and $SO_2$ each in gaseous state are readily removed outside the system in the stirring step, and the S is readily removed in the successive distillation step in the same manner as above described.

Now, a crude fluoroalkylsulfonic acid ($RfSO_3H$) produced by subjecting a corresponding potassium fluroalkysulfonate ($RfSO_3K$) to decomposition with sulfuric acid is sometimes contaminated with a trace amount of metal impurities other than the above-described impurities, such as Fe, Ni, Cr, and the like resulted from a reaction vessel itself used for the decomposition with sulfuric acid. According to the present invention, these metal impurities can be desirably removed in the distillation step.

In addition, in the case where the crude fluoroalkylsulfonic acid is refined in accordance with the second embodiment of the present invention, it is sometimes contaminated with a trace amount of metal impurities such as Al contained in the active silica used in the stirring treatment step. However, such metal impurities can be also desirably removed in the distillation step of the present invention.

In any of the first and second embodiments of the present invention, the stirring treatment step is conducted at a higher temperature than room temperature, specifically at a temperature of 60° C. to 300° C. and under condition of atmospheric pressure or reduced pressure while stirring the mixture, wherein gaseous materials occurred are removed outside the system in the stirring treatment step, as above described. In order to facilitate the removal of the gaseous materials, it is possible to blow appropriate gas, which is not reactive with the fluoroalkylsulfonic acid ($RfSO_3H$), into the mixture in the stirring treatment step. Specific examples of such gas are air, nitrogen gas, hydrogen gas, oxygen gas, inert gases such as argon gas and helium gas, and hydrocarbon gases such as methane gas and ethane gas, and carbon fluoride gases.

When the stirring treatment step is conducted at room temperature or less, the foregoing chemical reactions (8) to (13) do not efficiently proceed as desired and it takes a long period of time until the chemical reactions are completed. On the other hand, the stirring treatment step is conducted at a temperature of higher than 300° C., the fluoroalkylsulfonic acid ($RfSO_3H$) becomes liable to suffer from pyrolysis.

The period of time during which the stirring treatment step is conducted is also an important factor in the present invention. It is necessary for the stirring treatment step to be conducted for a period of time of at least 30 minutes. In the case where the period of time for the stirring treatment is less than 30 minutes, the foregoing reactions (8) to (13) are not sufficiently occurred.

The distillation step may be conducted by a simple distillation process. However, in order to attain a high refining efficiency, it is desired to be conducted in a manner of using a rectification tower or a plate type distillation tower.

The refining process comprising the foregoing stirring treatment step and distillation step according to the present invention may be conducted by a conventional apparatus comprising a reaction vessel provided with a stirring mechanism, a heat exchanging mechanism and a deaerating mechanism, which is capable of conducting the stirring treatment step, and a distillation vessel comprising a rectification mechanism or a distillation mechanism, a condensation mechanism, and a product-receiving mechanism, which is capable of conducting the distillation step.

The reaction vessel may be of the coil or jacket type. The reaction vessel is desired to one made of an acidproof and corrosion-resistant material such as stainless steel or one applied with a lining composed of an acidproof and corrosion resistant material such as Teflon (trademark name) to the inside thereof.

The rectification mechanism may be a rectification tower packed with a Raschig ring. The distillation mechanism may be a plate type distillation tower. In any case, the inside of the distillation vessel is desired to have a lining composed of an acidproof and corrosion resistant material such as glass, Teflon, or the like.

In the present invention, extremely high refinement can be attained for the resulting refined fluoroalkylsulfonic acid by terminating the distillation step when about 50 wt. % of the mixture dedicated for distillation is distilled. And it is possible to recycle the water contained in the residue on distillation resulted therein to the process of conducting sulfuric acid-decomposition for producing a crude fluoroalkylsulfonic acid.

In this case, it is possible to integrate the system for conducting the refining process with the process for producing a crude $RfSO_3H$ by way of the sulfuric acid-decomposition of a $RfSO_3K$ to be a complete closed system.

Now, the crude $RfSO_3H$ dedicated for the refining process according to the present invention may be produced by a conventional manner as described in Literature 1. That is, $RfSO_3K$ is firstly produced by way of the chemical reactions shown in the foregoing reaction formulas (2) and (3), the $RfSO_3K$ is reacted with concentrated sulfuric acid to obtain a mixture comprising $RfSO_3H$ and $KHSO_4$ as shown in the foregoing reaction formula (4), and the mixture is subjected to vacuum distillation, to thereby obtain a crude $RfSO_3H$.

Specifically, a crude trifluoromethanesulfonic acid as the crude $RfSO_3H$ may be produced in the following manner.

That is, $CH_3SO_2F$ is subjected to electrolytic fluorination using HF to obtain $CF_3SO_2F$. The resultant $CF_3SO_2F$ is subjected to hydrolysis using KOH to obtain $CF_3SO_3K$. The $CF_3SO_3K$ obtained is subjected to acid decomposition with the use of concentrated $H_2SO_4$ and if necessary, additionally fuming sulfuric acid at elevated temperature and under reduced pressure to obtain a $CF_3SO_3H$-containing reaction product. The reaction product obtained is subjected to simple distillation at a temperature of from 120° to 200° C. and under condition of reduced pressure of from 50 to 10 Torr to obtain a distillate of $CF_3SO_3H$. Thus, there is obtained a crude product of $CF_3SO_3H$. This $CF_3SO_3H$ product still contains a certain amount of those impurities as above described.

In the following, the advantages of the present invention will be described in more detail by reference to examples, which are provided here for illustrative purposes only, and are not intended to limit the scope of the present invention.

EXAMPLE 1

There was provided a crude potassium salt cake of the composition shown in Table 1.
(1) Production of crude $CF_3SO_3H$:

1000 Kg of the crude potassium salt cake, 1080 Kg of 97% $H_2SO_4$, 317 Kg of 25% fuming sulfuric acid (composed of 75% $H_2SO_4$ and 25% $SO_3$), and 20 Kg of powdery active silica were introduced into the conventional Teflon-lined reaction vessel provided with an agitator and a coil type heat exchanger, wherein they were mixed and subjected to chemical reaction (acid decomposition) at 120° C. for an hour while stirring the mixture. The mixture thus treated was subjected to simple distillation at a reduced pressure of from 50 to 10 Torr and under condition of 120° to 200° C. for the temperature of the mixture, to thereby obtain 669 Kg of a distillate of $CF_3SO_3H$.

A specimen of the resultant $CF_3SO_3H$ product was subjected to quantitative analysis. As a result, the resultant $CF_3SO_3H$ was found to contain more than 99.0 wt. % of $CF_3SO_3H$, 0.5 wt. % of $H_2SO_4$, 500 wt.ppm of free fluorine, and 50 wt.ppm of water ($H_2O$). (This $CF_3SO_3H$ product will be hereinafter referred to as "crude $CF_3SO_3H$ product")
(2) Refinement:

105 Kg of the crude $CF_3SO_3H$ product, 1 Kg of water, and 400 g of powdery active silica were introduced into the Teflon-lined reaction vessel for conducting the stirring treatment step, provided with an agitator, a jacket type heat exchanger and a deaerating mechanism, wherein they were mixed and stirred for 30 minutes under condition of atmospheric pressure while maintaining the mixture at 80 ° C.

The thus treated mixture was introduced into the distillation vessel comprising a distillation mechanism, a condensation mechanism, and a product-receiving mechanism, wherein it was subjected to simple vacuum distillation at a reduced pressure of 25 Torr and under condition of from 85° to 95° C. for the temperature of the mixture while stirring the mixture, to thereby obtain 75 Kg of a distillate product of $CF_3SO_3H$.

A specimen of the resultant distillate product of $CF_3SO_3H$ was subjected to quantitative analysis in order to examine impurities contained therein. As a result, it was found to contain less than 2 wt.ppm of sulfuric acid ($H_2SO_4$), less than 2 wt.ppm of free fluorine component, and 150 wt.ppm of water ($H_2O$).

The $CF_3SO_3H$ thus obtained was reacted with $Li_2CO_3$ to obtain $CF_3SO_3Li$. The resultant $CF_3SO_3Li$ was examined as for its purity, and as a result, it was found that the $CF_3SO_3Li$ is of extremely high purity.

Using this $CF_3SO_3Li$, there was prepared an electrolyte for a lithium battery. The resultant electrolyte was examined, and as a result, it was found to be of an extremely high quality.

EXAMPLE 2

The procedures of Example 1 were repeated, except that in the refinement step (2), the amount of the water used was changed to 28 Kg, to thereby obtain a refined product of $CF_3SO_3H$.

A specimen of the resultant product of $CF_3SO_3H$ was subjected to quantitative analysis in order to examine impurities contained therein. As a result, it was found to contain 6 wt.ppm of sulfuric acid ($H_2SO_4$), less than 2 wt.ppm of free fluorine component, and about 33 wt. % of water ($H_2O$).

Using the $CF_3SO_3H$ thus obtained, there was prepared an electrolyte for a lithium battery in the same manner as in Example 1. The resultant electrolyte was examined, and as a result, it was found to be satisfactory in terms of the quality.

EXAMPLE 3

The procedures of Example 1 were repeated, except that in the refinement step (2), the amount of the water used was changed to 0.1Kg, to thereby obtain a refined product of $CF_3SO_3H$.

A specimen of the resultant product of $CF_3SO_3H$ was subjected to quantitative analysis in order to examine impurities contained therein. As a result, it was found to contain 0.29 wt. % of sulfuric acid ($H_2SO_4$), 10 wt.ppm of free fluorine component, and 50 wt.ppm of water ($H_2O$).

The refined product of $CF_3SO_3H$ obtained contains a relatively large amount of sulfuric acid, but it is not a problematic amount. And the refined product is extremely slight in terms of the contamination of free fluorine component, and in addition, the water content thereof is desirably slight.

Thus, it is understood that the refined product of $CF_3SO_3H$ obtained is not sufficient enough in terms of the purity for use as the starting material in the production of a high purity $CF_3SO_3Li$ to be used for an electrolyte of a lithium battery but it can be desirably used, for example, as a catalyst in various organic synthesis reactions.

EXAMPLE 4

In this example, as the crude $CF_3SO_3H$ to be refined by the process of the present invention, there was intentionally used a crude $CF_3SO_3H$ sample with a trace contamination of free fluorine component and water and with a relatively large contamination of sulfuric acid in order to examine the sulfuric acid-removing effects of the process according to the present invention.

That is, there was firstly provided a commercially available $CF_3SO_3H$ product containing 6 wt.ppm of free fluorine component and 150 wt.ppm of water (product by Central Glass Co., Ltd.).

Then, 178.3 Kg of the $CF_3SO_3H$ product, 20.7 Kg of 97% $H_2SO_4$, 11.0 Kg of 25% fuming sulfuric acid were introduced into the conventional Teflon-lined reaction vessel provided with an agitator and a coil type heat exchanger, wherein they were mixed while stirring the mixture, whereby 210 Kg of a crude $CF_3SO_3H$ sample containing 15.1 wt. % of $H_2SO_4$, 5 wt.ppm of free fluorine component, and 130 wt.ppm of water ($H_2O$) was obtained.

The resultant crude $CF_3SO_3H$ in an amount of 210 Kg, and 6.1Kg of water were introduced into the Teflon-lined reaction vessel for conducting the stirring treatment step, provided with an agitator, a jacket type heat exchanger and a deaerating mechanism, wherein they were mixed and stirred for 30 minutes under condition of atmospheric pressure while maintaining the mixture at 300° C. In this case, no powdery activated silica was used.

The thus treated mixture was introduced into the distillation vessel comprising a distillation mechanism, a condensation mechanism, and a product-receiving mechanism, wherein it was subjected to simple vacuum distillation at a reduced pressure of 30 Torr and under condition of from 90° to 100° C. for the temperature of the mixture while stirring the mixture, to thereby obtain 100 Kg of a distillate product of $CF_3SO_3H$.

A specimen of the resultant product of $CF_3SO_3H$ was subjected to quantitative analysis in order to examine impurities contained therein. As a result, the product of $CF_3SO_3H$ was found to contain 20 wt.ppm of sulfuric acid ($H_2SO_4$), 5 wt.ppm of free fluorine component, and 100 wt.ppm of water ($H_2O$).

Based on the result, it is understood that the process according to the present invention provides a significant sulfuric acid-removing effect even in the case where no activated silica is used.

EXAMPLE 5

In general, in the case of subjecting crude $CF_3SO_3K$ to sulfuric acid-decomposition to obtain crude $CF_3SO_3H$, when in addition to concentrated sulfuric acid, fuming sulfuric acid is used in an amount of more than necessary, the amount of sulfur trioxide present in the system becomes excessive to cause various side reactions. Because of this, even after simple distillation having been conducted, the resulting refined $CF_3SO_3H$ is still contaminated with $SO_3$, $S_2O_3$, and $CF_3SO_2.OCF_3$ caused by said side reactions, other than contaminants such as $H_2SO_4$ and free fluorine components. In this case, if the above sulfuric acid-decomposition of the crude $CF_3SO_3K$ is conducted in a non-lined reaction vessel made of stainless steel, the resulting refined $CF_3SO_3K$ is liable to be additionally contaminated with metal components of Fe, Cr, Ni, and the like resulted from the reaction vessel itself upon the sulfuric acid-decomposition.

Incidentally, the optimum amount of the fuming sulfuric acid to be used upon conducting the sulfuric acid-decomposition of the crude $CF_3SO_3K$ is somewhat different depending upon the water content of a crude $CF_3SO_3K$ used as the starting material.

In this example, in order to examine whether or not a crude $CF_3SO_3H$ product containing those impurities as above described can be refined as desired by the process of the present invention, there was intentionally used, as the crude $RfSO_3H$ to be refined, a specific crude $CF_3SO_3H$ product contaminated with various impurities obtained by subjecting a corresponding $CF_3SO_3K$ product to sulfuric acid-decomposition using fuming sulfuric acid in an excessive amount corresponding to 130% of the optimum amount in a non-lined reaction vessel made of stainless steel.

This example was conducted as follows.
(1) Production of crude $CF_3SO_3H$:

There was provided a crude potassium salt cake of the composition shown in Table 1.

1000 Kg of the crude potassium salt cake, 1080 Kg of 97% $H_2SO_4$, 412 Kg of 25% fuming sulfuric acid, and 20 Kg of powdery active silica were introduced into the conventional non-lined reaction vessel made of stainless steel and provided with an agitator and a jacket type heat exchanger, wherein they were mixed and subjected to chemical reaction (acid decomposition) at 120° C. for an hour while stirring the mixture. The resultant obtained was subjected to simple distillation at a reduced pressure of from 50 to 10 Torr and under condition of from 120° to 200° C. for the temperature of the mixture while stirring the mixture, to thereby obtain 602 Kg of a blueish-green colored distillate of $CF_3SO_3H$.

A specimen of the resultant $CF_3SO_3H$ product was subjected to quantitative analysis. As a result, the resultant $CF_3SO_3H$ was found to contain 87.6 wt. % of $CF_3SO_3H$, 10.0 wt. % of $H_2SO_4$, 1050 wt.ppm of free fluorine component, 0 wt.ppm of water ($H_2O$), 45 wt.ppm of $S_2O_3$, 2050 wt.ppm of $SO_3$, 2 wt. % of $CF_3SO_2.OCF_3$, 10 wt.ppm of Fe, 5 wt.ppm of Cr, 5 wt.ppm of Ni, 250 wt.ppm of Na, and 500 wt.ppm of K. (this $CF_3SO_3H$ product will be hereinafter referred to as "crude $CF_3SO_3H$ product").
(2) Refinement:

310 Kg of the crude $CF_3SO_3H$ product, 10.1Kg of water, and 1.2 Kg of powdery active silica were introduced into the non-lined reaction vessel made of stainless steel for conducting the stirring treatment step, provided with an agitator, a jacket type heat exchanger and a deaerating mechanism, wherein they were mixed and stirred for 5 hours under reduced pressure condition of 30 Torr while maintaining the mixture at 150° C. and while blowing nitrogen gas into the mixture at a flow rate of 2 Nl (normal liter)/minute.

The thus treated mixture was introduced into the distillation vessel comprising a distillation mechanism, a condensation mechanism, and a product-receiving mechanism, wherein it was subjected to simple vacuum distillation at a reduced pressure of 35 Torr and under condition of from 90° to 105° C. while stirring the mixture, to thereby obtain 140 Kg of a colorless distillate product of $CF_3SO_3H$.

A specimen of the resultant distillate product of $CF_3SO_3H$ was subjected to quantitative analysis. As a result, the $CF_3SO_3H$ product was found to contain more than 99.0 wt. % of $CF_3SO_3H$, 7 wt.ppm of $H_2SO_4$, 5 wt.ppm of free fluorine component, 250 wt.ppm of water ($H_2O$), less than 1.2 wt.ppm of S, less than 0.5 wt. % of $CF_3SO_2.OCF_3$, less than 0.08 wt.ppm of Fe, less than 0.03 wt.ppm of Cr, less than 0.1 wt.ppm of Ni, less than 0.2 wt.ppm of Na, and less than 0.3 wt.ppm of K.

Thus, it is understood that a crude $CF_3SO_3H$ containing a distinguishable amount of various contaminants including metal components can be markedly refined according to the present invention.

EXAMPLE 6

(1) Production of crude $CF_3SO_3H$

The production step (1) in Example 1 were repeated, to thereby obtain 669 Kg of a distillate of $CF_3SO_3H$.

A specimen of the resultant $CF_3SO_3H$ product was subjected to quantitative analysis. As a result, the composition of the resultant $CF_3SO_3H$ product was found to be substantially the same as that of the $CF_3SO_3H$ distillate product obtained in Example 1.

(2) Refinement:

51Kg of the crude $CF_3SO_3H$ product obtained in the above, 5.5 Kg of water, and 3.6 Kg of powdery active silica were introduced into the Teflon-lined reaction vessel for conducting the stirring treatment step, provided with an agitator, a jacket type heat exchanger and a deaerating mechanism, wherein they were mixed and stirred for 30 minutes under condition of atmospheric pressure while maintaining the mixture at 80° C.

The thus treated mixture was introduced into the distillation vessel comprising a distillation mechanism, a condensation mechanism, and a product-receiving mechanism, wherein it was subjected to simple vacuum distillation at a reduced pressure of 25 Torr and under condition of from 85° to 95° C. for the temperature of the mixture while stirring the mixture, to thereby obtain 35 Kg of a distillate product of $CF_3SO_3H$.

A specimen of the resultant distillate product of $CF_3SO_3H$ was subjected to quantitative analysis in order to examine impurities contained therein. As a result, it was found to contain less than 2 wt.ppm of sulfuric acid ($H_2SO_4$), less than 2 wt.ppm of free fluorine component, and 450 wt.ppm of water ($H_2O$).

Using the $CF_3SO_3H$ thus obtained, there was prepared an electrolyte for a lithium battery in the same manner as in Example 1. The resultant electrolyte was examined, and as a result, it was found to be satisfactory in terms of the quality.

EXAMPLE 7

(1) Production of crude $CF_3SO_3H$:

There was provided a crude potassium salt cake of the composition shown in Table 2.

100 Kg of the crude potassium salt cake, 444 Kg of 97% $H_2SO_4$, 286 Kg of 25% fuming sulfuric acid, and 1.9 Kg of powdery active silica were introduced into the conventional non-lined reaction vessel made of stainless steel and provided with an agitator and a jacket type heat exchanger, wherein they were mixed and subjected to chemical reaction (acid decomposition) at 120° C. for an hour while stirring the mixture.

The resultant decomposed product was subjected to simple distillation at a reduced pressure of from 50 to 10 Torr and under condition of from 160° to 240° C. for the temperature of the decomposed product, to thereby obtain 73.1Kg of a distillate of n-$C_4F_9SO_3H$.

A specimen of the resultant n-$C_4F_9SO_3H$ product was subjected to quantitative analysis in order to examine impurities contained therein. As a result, the n-$C_4F_9SO_3H$ product was found to not contain any metal component of the constituent Fe, Cr, Ni, or the like of the stainless steel reaction vessel but to contain 5 wt. % of $H_2SO_4$ and 1010 wt.ppm of fluorine component. (This n-$C_4F_9SO_3H$ product will be hereinafter referred to as "crude n-$C_4F_9SO_3H$ product").

As for the reason why the crude n-$C_4F_9SO_3H$ product is free of such metal component in spite of having used the non-lined stainless steel reaction vessel upon the sulfuric acid-decomposition of the n-$C_4F_9SO_3K$ is considered, it is considered that the stainless steel reaction vessel was not suffered from corrosion because the amount of the fuming sulfuric acid used was optimum in terms of the amount of sulfur trioxide in relation to the water content in the reaction system.

(2) Refinement:

10 Kg of the crude n-$C_4F_9SO_3H$ product, 0.1 Kg of water, and 150 g of powdery active silica were introduced into the non-lined reaction vessel made of stainless steel for conducting the stirring treatment step, provided with an agitator, a jacket type heat exchanger and a deaerating mechanism, wherein they were mixed and stirred for an hour under condition of atmospheric pressure while maintaining the mixture at 80° C.

The thus treated mixture was introduced into the distillation vessel comprising a distillation mechanism, a condensation mechanism, and a product-receiving mechanism, wherein it was subjected to simple vacuum distillation at a reduced pressure of 10 Torr and under condition of from 130° to 140° C. for the temperature of the mixture while stirring the mixture, to thereby obtain 7.1 Kg of a distillate product of n-$C_4F_9SO_3H$.

A specimen of the resultant distillate product of n-$C_4F_9SO_3H$ was subjected to quantitative analysis in order to examine impurities contained therein. As a result, it was found to contain less than 2 wt.ppm of sulfuric acid ($H_2SO_4$), less than 2 wt.ppm of free fluorine component, and 1.4 wt. % of water ($H_2O$).

Thus, it is understood that the resultant refined n-$C_4F_9SO_3H$ product is of markedly high purity.

COMPARATIVE EXAMPLE 1

The procedures of Example 1 were repeated, except that in the stirring treatment step of the refinement (2), the addition of the water was not conducted, to thereby obtain 75 Kg of a refined product of $CF_3SO_3H$.

A specimen of the resultant product of $CF_3SO_3H$ was subjected to quantitative analysis in order to examine impurities contained therein. As a result, it was found to contain 0.55 wt. % of sulfuric acid ($H_2SO_4$), 30 wt.ppm of free fluorine component, and 150 wt.ppm of water ($H_2O$).

This $CF_3SO_3H$ product was compared with that obtained in Example 1 in terms of the impurity content. As a result, it was found that the $CF_3SO_3H$ product obtained in this comparative example is apparently inferior to that obtained in Example 1 particularly in terms of the contamination of $H_2SO_4$.

It is apparently understood that the reason for this is due to that no water was used in the stirring treatment step.

Although the refined $CF_3SO_3H$ product obtained in this comparative example is not sufficient enough in terms of the purity, it seems possible to be used as a catalyst in certain organic synthesis reactions.

COMPARATIVE EXAMPLE 2

The procedures of Example 1 were repeated, except that in the stirring treatment step of the refinement (2), neither the powdery active silica nor the water were used, to thereby obtain 75 Kg of a refined product of $CF_3SO_3H$.

A specimen of the resultant product of $CF_3SO_3H$ was subjected to quantitative analysis in order to examine impurities contained therein. As a result, it was found to contain 0.54 wt. % of sulfuric acid ($H_2SO_4$), 450 wt.ppm of free fluorine component, and 100 wt.ppm of water ($H_2O$).

This $CF_3SO_3H$ product was compared with that obtained in Example 1 in terms of the impurity content. As a result, it was found that the $CF_3SO_3H$ product obtained in this comparative example is apparently inferior to that obtained in Example 1 in terms of the contamination of not only $H_2SO_4$ but also free fluorine component.

It is apparently understood that the reason for this is due to that neither activated silica nor water were used in the stirring treatment step.

The refined $CF_3SO_3H$ product obtained in this comparative example is apparently inferior in terms of the purity, and because of this, it cannot be used even as a catalyst in organic synthesis reactions.

COMPARATIVE EXAMPLE 3

The procedures of Example 1 were repeated, except that in the stirring treatment step of the refinement (2), the amount of the water was changed to 53 g and no powdery activated silica was used, to thereby obtain 75 Kg of a refined product of $CF_3SO_3H$.

A specimen of the resultant product of $CF_3SO_3H$ was subjected to quantitative analysis in order to examine impurities contained therein. As a result, it was found to contain 0.47 wt. % of sulfuric acid ($H_2SO_4$), 400 wt.ppm of free fluorine component, and 150 wt.ppm of water ($H_2O$).

This $CF_3SO_3H$ product was compared with that obtained in Example 1 in terms of the impurity content. As a result, it was found that the $CF_3SO_3H$ product obtained in this comparative example is apparently inferior to that obtained in Example 1 in terms of the contamination of not only $H_2SO_4$ but also free fluorine component.

It is apparently understood that the reason for this is due to that an excessive amount of water was used without using powdery activated silica in the stirring treatment step.

The refined $CF_3SO_3H$ product obtained in this comparative example is apparently inferior in terms of the purity, and because of this, it cannot be used even as a catalyst in organic synthesis reactions.

COMPARATIVE EXAMPLE 4

The procedures of Example 1 were repeated, except that in the stirring treatment step of the refinement (2), the amount of the water was changed to 56.5 Kg and no powdery active silica was used, to thereby obtain 75 Kg of a refined product of $CF_3SO_3H$.

A specimen of the resultant product of $CF_3SO_3H$ was subjected to quantitative analysis in order to examine impurities contained therein. As a result, it was found to contain 0.25 wt. % of sulfuric acid ($H_2SO_4$), 300 wt.ppm of free fluorine component, and 66.7 wt. % of water ($H_2O$).

This $CF_3SO_3H$ product was compared with that obtained in Example 1 in terms of the impurity content. As a result, it was found that the $CF_3SO_3H$ product obtained in this comparative example is apparently inferior to that obtained in Example 1 in terms of the contamination of not only $H_2SO_4$ but also free fluorine component.

It is apparently understood that the reason for this is due to that an excessive amount of water was used without using powdery activated silica in the stirring treatment step.

The refined $CF_3SO_3H$ product obtained in this comparative example is apparently inferior in terms of the purity, and because of this, it cannot be used even as a catalyst in organic synthesis reactions.

TABLE 1

| crude potassium salt cake | | |
|---|---|---|
| | kg | wt % |
| $CF_3SO_3K$ | 916.0 | 91.6 |
| KOH | 12.0 | 1.2 |
| KF | 5.0 | 0.5 |
| NaF | 9.0 | 0.9 |
| $K_2SO_4$ | 27.0 | 2.7 |
| $H_2O$ | 31.0 | 3.1 |
| Total | 1000.0 | 100.0 |

TABLE 2

| crude potassium salt cake | | |
|---|---|---|
| | kg | wt % |
| n-$C_4F_9SO_3K$ | 91.5 | 91.5 |
| KOH | 1.5 | 1.5 |
| KF | 0.7 | 0.7 |
| NaF | 0.8 | 0.8 |
| $K_2SO_4$ | 3.5 | 3.5 |
| $H_2O$ | 2.0 | 2.0 |
| Total | 100.0 | 100.0 |

What we claim is:

1. A process for refining a fluoroalkylsulfonic acid in a crude state which is represented by the general formula RfSO$_3$H, with Rf being a fluoroalkyl group having 1 to 4 carbon atoms, into a highly refined fluoroalkylsulfonic acid substantially free of impurities, said process comprising the steps of:

(a) providing said fluoroalkylsulfonic acid in a crude state, (b) mixing said fluoroalkylsulfonic acid in a crude state with water in an amount of 0.1 wt. % to 30 wt. % versus the total amount of said fluoroalkylsulfonic acid and said water to obtain a mixture, (c) stirring said mixture while maintaining said mixture at a temperature which is higher than room temperature, and (d) subjecting the mixture treated in said step (c) to distillation.

2. A process according to claim 1, wherein the impurities include sulfuric acid and free fluorine components.

3. A process according to claim 2, wherein the impurities further include metals.

4. A process according to claim 1, wherein said crude fluoroalkylsulfonic acid is one obtained by subjecting a potassium fluoroalkylsulfonate represented by the general formula $RfSO_3K$ with Rf being a fluoroalkyl group having 1 to 4 carbon atoms to acid decomposition with the use of sulfuric acid.

5. A process according to claim 1, wherein the temperature in step (c) is in the range of from 60° C. to 300° C.

6. A process according to claim 1, wherein the step (c) is conducted for a period of 30 minutes or more.

7. A process according to claim 1, wherein the step (c) is conducted under condition of atmospheric pressure or reduced pressure.

8. A process according to claim 1, wherein the step (c) is conducted while blowing a gas which is not reactive with the fluoroalkylsulfonic acid into the mixture.

9. A process according to claim 8, wherein the gas is a gas selected from the group consisting of air, oxygen gas, hydrogen gas, nitrogen gas, inert gases, hydrocarbon gases, and carbon fluoride gases.

10. A process according to claim 1, wherein the crude fluoroalkylsulfonic acid is trifluoromethanesulfonic acid.

11. A process for refining a fluoroalkylsulfonic acid in a crude state which is represented by the general formula $RfSO_3H$, with Rf being a fluoroalkyl group having 1 to 4 carbon atoms, into a highly refined fluoroalkylsulfonic acid substantially free of impurities, said process comprising the steps of:

(a) providing said fluoroalkylsulfonic acid in a crude state, (b) mixing said fluoroalkylsulfonic acid in a crude state with an active silica and water in an amount of 0.1 wt. % to 30 wt. % versus the total amount of said fluoroalkylsulfonic acid, said active silica and said water to obtain a mixture, (c) stirring said mixture while maintaining said mixture at a temperature which is higher than room temperature, and (d) subjecting the mixture treated in said step (c) to distillation.

12. A process according to claim 11, wherein the impurities include sulfuric acid and free fluorine components.

13. A process according to claim 11, wherein the impurities further include metals.

14. A process according to claim 11, wherein the crude fluoroalkylsulfonic acid is one obtained by subjecting a potassium fluoroalkylsulfonate represented by the general formula $RfSO_3K$ with Rf being a fluoroalkyl group having 1 to 4 carbon atoms to acid decomposition with the use of sulfuric acid.

15. A process according to claim 11, wherein the active silica used in the step (b) is a material selected from the group consisting of silica compounds obtained from diatomaceous earth materials, sodium silicate, siliconfluoride, sodium siliconfluoride, and mixtures of these compounds.

16. A process according to claim 11, wherein as the active silica used in the step (b), a glassy material is used.

17. A process according to claim 15, wherein the activated silica is in a powdery form.

18. A process according to claim 11, wherein the active silica used in the step (b) is in an amount corresponding to a figure of 2 to 100 in terms of the reaction equivalent weight ratio of $SiO_2/4HF$ in the chemical reaction represented by the reaction formula $SiO_2+4HF \rightarrow 2H_2O+SiF_4$, wherein $SiO_2$ indicates an activated silica and HF indicates a free fluorine component contained in the crude fluoroalkylsulfonic acid.

19. A process according to claim 11, wherein the temperature is in the range of from 60° C. to 300° C.

20. A process according to claim 11, wherein the step (c) is conducted for a period of 30 minutes or more.

21. A process according to claim 11, wherein the step (c) is conducted under condition of atmospheric pressure or reduced pressure.

22. A process according to claim 11, wherein the step (c) is conducted while blowing a gas which is not reactive with the fluoroalkylsulfonic acid into the mixture.

23. A process according to claim 22, wherein the gas is a gas selected from the group consisting of air, oxygen gas, hydrogen gas, nitrogen gas, inert gases, hydrocarbon gases, and carbon fluoride gases.

24. A process according to claim 11, wherein the crude fluoroalkylsulfonic acid is trifluoromethanesulfonic acid.

* * * * *